United States Patent [19]
Scaria et al.

[11] Patent Number: 6,020,191
[45] Date of Patent: Feb. 1, 2000

[54] ADENOVIRAL VECTORS CAPABLE OF FACILITATING INCREASED PERSISTENCE OF TRANSGENE EXPRESSION

[75] Inventors: Abraham Scaria, Framingham; Richard J. Gregory, Westford; Samuel C. Wadsworth, Shrewsbury, all of Mass.

[73] Assignee: Genzyme Corporation, Cambridge, Mass.

[21] Appl. No.: 08/839,553

[22] Filed: Apr. 14, 1997

[51] Int. Cl.$^7$ .................................................. C12N 15/86
[52] U.S. Cl. ........................................ 435/320.1; 536/23.5
[58] Field of Search ............................. 435/172.1, 172.3, 435/320.1, 455, 456; 424/93.2, 93.6; 536/23.1, 23.5

[56] References Cited

U.S. PATENT DOCUMENTS 5,747,469  5/1998  Roth et al. ................................. 514/44

FOREIGN PATENT DOCUMENTS

| | | |
|---|---|---|
| 0707071 | 5/1996 | European Pat. Off. . |
| WO 9428938 | 12/1994 | WIPO . |
| WO 9618372 | 6/1996 | WIPO . |
| WO 9630534 | 10/1996 | WIPO . |
| WO 9708298 | 3/1997 | WIPO . |

OTHER PUBLICATIONS

Verma et al., Nature, vol. 389, pp. 239–242, Sep. 18, 1997.
Lee et al., Gene Therapy, vol. 2, pp. 256–262, 1995.
Orkin et al., "Report and Recommendations of the Panel to Assess the NIH Investment in Research on Gene Therapy", Dec. 7, 1995.
Berkner, K.L., Curr. Top. Micro. Immunol. 158:39–66, 1992.
Graham, F.L., J. Gen. Virol. 36:59–72, 1977.
Zhou et al., J. Virol. 70:7030–7038, 1996.
Krougliak et al., Hum. Gene Ther. 6:1575–1586, 1995.
Caravokyri et al., J. Virol. 69:6627–6633, 1995.
Kochanek et al., Proc. Natl. Acad. Sci. USA 93:5731–5736, 1996.
Fisher et al., Virology 217:11–22, 1996.
Wills et al., Hum. Gene Ther. 5:1079–188, 1994.
Vincent et al., Nature Genetics 5:130–134, 1993.
Descamps et al., Hum. Gene Ther. 5:979–985, 1994.
Stratford–Perricaudet et al., Hum. Gene Ther. 1:241–256, 1990.
Mitani et al., Hum. Gene Ther. 5:941–948, 1994.
Haddada et al., Hum. Gene Ther. 4:703–711, 1993.
Jaffe et al., Nature Genetics 1:372–378, 1992.
Ohwada et al., Blood 88:778–784, 1996.
Ohwada et al., Hum. Gene Ther. 7:1567–1576, 1996.
Zabner et al., Nature Genetics 6:75–83, 1994.
Rich et al., Hum. Gene Ther. 4:461–476, 1993.
Zabner et al., Cell 75:207–216, 1993.
Crystal et al., Nature Genetics 8:42–51, 1994.
Zabner et al., J. Clin. Invest. 97:1504–1511, 1996.
Yang et al., J. Virol. 69:2004–2015, 1995.
Yang et al., Proc. Natl. Acad. Sci. USA 91:4407–4411, 1994.
Zsengeller et al., Hum Gene Ther. 6:457–467, 1995.
Worgall et al., Hum. Gene Ther. 8:37–44, 1997.
Kaplan et al., Hum. Gene Ther. 8:45–56, 1997.
Smith, G.L., Trends Microbiol. 2:81–88, 1994.
Crystal, R., Science 270:404–410, 1995.
Fang et al., Hum. Gene Ther. 6:1039–1044, 1995.
Kay et al., Nature Genetics 11:191–197, 1995.
Mack et al., Hum. Gene Ther. 8:99–109, 1997.
Barr et al., Gene Ther. 2:151–155, 1995.
Guo et al., Gene Ther. 3:802–801, 1996.
Tripathy et al., Nature Med. 2:545–550, 1996.
Yang et al., Nature Genetics 7:362–369, 1994.
Lieber et al., J. Virol. 70:8944–8960, 1996.
Gorziglia et al., J. Virol. 70:4173–4178, 1996.
Brody et al., Hum. Gene Ther. 5:821–836, 1994.
Wold et al., Trends Microbiol. 2:437–443, 1994.
Tollefson et al., J. Virol. 70:2296–2306, 1996.
Tollefson et al., Virology 220:152–162, 1996.
Armentano et al., Hum. Gene Ther. 6:1343–1353, 1995.
Armentano et al., J. Virol. 71:2408–2416, 1997.
Hehir et al., J. Virol. 70:8459–8467, 1996.
Ginsberg et al., Proc. Natl. Acad. Sci. USA 88:1651–1655, 1991.
Sparer, T.E. et al., Generation of cytotoxic T lymphocytes, J. Virol. 71:2277–2284, 1997.
Scaria et al., J. Virol, vol. 72, No. 9, pp. 7302–7309, Sep. 1998.

*Primary Examiner*—David Guzo
*Attorney, Agent, or Firm*—Baker and Botts, L.L.P.

[57] ABSTRACT

The invention is directed to novel adenoviral vectors which are capable of facilitating persistent expression of a transgene which is delivered by the vector to a cell. The vectors are E1/partial E3 deleted vectors which contain a transgene operably linked to expression control sequences, preferably the CMV promoter. The invention is also directed to compositions comprising the adenoviral vectors of the invention and to methods for providing persistent expression of a transgene to the cells of an individual by administration of the compositions.

3 Claims, 3 Drawing Sheets

ADENOVIRAL VECTORS CAPABLE OF FACILITATING INCREASED PERSISTENCE OF TRANSGENE EXPRESSION

The invention is directed to novel adenoviral vectors which are capable of facilitating persistent expression of a transgene which is delivered by the vector to a cell. The vectors are E1/partial E3 deleted vectors which contain a transgene operably linked to expression control sequences, preferably the CMV promoter. The invention is also directed to compositions comprising the adenoviral vectors of the invention and to methods for providing persistent expression of a transgene to the cells of an individual by administration of the compositions.

BACKGROUND OF THE INVENTION

Adenovirus is a non-enveloped, nuclear DNA virus with a genome of about 36 kb, which has been well-characterized through studies in classical genetics and molecular biology (Horwitz, M. S., "Adenoviridae and Their Replication," in *Virology*, 2nd edition, Fields et al., eds., Raven Press, New York, 1990). The viral genes are classified into early (known as E1–E4) and late (known as L1–L5) transcriptional units, referring to the generation of two temporal classes of viral proteins. The demarcation between these events is viral DNA replication.

Recombinant adenoviruses have several advantages for use as gene transfer vectors, including tropism for both dividing and non-dividing cells, minimal pathogenic potential, ability to replicate to high titer for preparation of vector stocks, and the potential to carry large inserts (Berkner, K. L., Curr. Top. Micro. Immunol. 158:39–66, 1992; Jolly, D., Cancer Gene Ther. 1:51–64, 1994).

The cloning capacity of an adenoviral vector is proportional to the size of the adenovirus genome present in the vector. For example, a cloning capacity of about 8 kb can be created from the deletion of certain regions of the virus genome dispensable for virus growth, e.g., E3, and the deletion of a genomic region such as E1 whose function may be restored in trans from 293 cells (Graham, F. L., J. Gen. Virol. 36:59–72, 1977) or A549 cells (Imler et al., Gene Ther. 3:75–84, 1996). Such E1-deleted vectors are rendered replication-defective. The upper limit of vector DNA capacity is about 105%–108% of the length of the wild-type genome. Further adenovirus genomic modifications are possible in vector design using cell lines which supply other viral gene products in trans, e.g., complementation of E2a (Zhou et al., J. Virol. 70:7030–7038, 1996), complementation of E4 (Krougliak et al., Hum. Gene Ther. 6:1575–1586, 1995; Wang et al., Gene Ther. 2:775–783, 1995), or complementation of protein IX (Caravokyri et al., J. Virol. 69:6627–6633, 1995; Krougliak et al., Hum. Gene Ther. 6:1575–1586, 1995). Maximum carrying capacity can be achieved using adenoviral vectors deleted for all viral coding sequences (Kochanek et al., Proc. Natl. Acad. Sci. USA 93:5731–5736, 1996; Fisher et al., Virology 217:11–22, 1996).

Transgenes that have been expressed to date by adenoviral vectors include p53 (Wills et al., Hum. Gene Ther. 5:1079–188, 1994); dystrophin (Vincent et al., Nature Genetics 5:130–134, 1993; erythropoietin (Descamps et al., Hum. Gene Ther. 5:979–985, 1994; ornithine transcarbamylase (Stratford-Perricaudet et al., Hum. Gene Ther. 1:241–256, 1990; We et al., J. Biol. Chem. 271;3639–3646, 1996;); adenosine deaminase (Mitani et al., Hum. Gene Ther. 5:941–948, 1994); interleukin-2 (Haddada et al., Hum. Genie Ther. 4:703–711, 1993); and α1-antitrypsin (Jaffe et al., Nature Genetics 1:372–378, 1992); thrombopoictin (Ohwada et al., Blood 88:778–784, 1996); and cytosine deaminase (Ohwada et al., Hum. Gene Ther. 7:1567–1576, 1996).

The tropism of adenoviruses for cells of the respiratory tract has particular relevance to the use of adenovirus in Gene Ther. for cystic fibrosis (CF), which is the most common autosomal recessive disease in Caucasians. Mutations in the cystic fibrosis transmembrane conductance regulator (CFTR) gene that disturb the cAMP-regulated Cl⁻ channel in airway epithelia result in pulmonary dysfunction (Zabner et al., Nature Genetics 6:75–83, 1994). Adenoviral vectors engineered to carry the CFTR gene have been developed (Rich et al., Hum. Gene Ther. 4:461–476, 1993) and studies have shown the ability of these vectors to deliver CFTR to nasal epithelia of CF patients (Zabner et al., Cell 75:207–216, 1993), the airway epithelia of cotton rats and primates (Zabner et al., Nature Genetics 6:75–83, 1994), and the respiratory epithelium of CF patients (Crystal et al., Nature Genetics 8:42–51, 1994). Recent studies have shown that administering an adenoviral vector containing a DNA sequence encoding CFTR to airway epithelial cells of CF patients can restore a functioning chloride ion channel in the treated epithelial cells (Zabner et al., J. Clin. Invest. 97:1504–1511, 1996).

The use of adenoviral vectors in gene transfer studies to date indicates that persistence of transgene expression is often transient. At least some of the limitation is due to the generation of a host immune response to the viral proteins which are expressed antigenically even from a replication-defective vector, triggering a pathological inflammatory response which may destroy or adversely affect the adenovirus-infected cells (Yang et al., J. Virol. 69:2004–2015, 1995; Yang et al., Proc. Natl. Acad. Sci. USA 91:4407–4411, 1994; Zsengeller et al., Hum Gene Ther. 6:457–467, 1995; Worgall et al., Hum. Gene Ther. 8:37–44, 1997; Kaplan et al., Hum. Gene Ther. 8:45–56, 1997). Immunologic reactions by the host to adenovirus infection include, inter alia, the generation of cytotoxic T-lymphocytes (CTL) which lyse infected cells displaying a viral antigen, cytolysis of virus-infected cells by tumor necrosis factor (TNF), synthesis of interferons, induction of apoptosis, production of antibodies, and other immunologic mechanisms (Smith, G. L., Trends Microbiol. 2:81–88, 1994). Because adenovirus does not integrate into the cell genome, host immune responses that destroy virions or infected cells have the potential to limit adenovirus-based gene delivery. An adverse immune response poses a serious obstacle for high dose administration of an adenoviral vector or for repeated administration (Crystal, R., Science 270:404–410, 1995).

In order to circumvent the host immune response which limits the persistence of transgene expression, various strategies have been employed, generally involving either the modulation of the immune response itself or the engineering of a vector that decreases the immune response.

The administration of immunosuppressive agents together with an adenoviral vector has been shown to prolong transgenc persistence (Fang et al., Hum. Gene Ther. 6:1039–1044, 1995; Kay et al., Nature Genetics 11:191–197, 1995; Zsellenger et al., Hum. Gene Ther. 6:457–467, 1995).

The administration of adenoviral vectors with alternating serotypes has shown some circumvention of the host immune response (Mack et al., Hum. Gene Ther. 8:99–109, 1997). Animal model studies have shown that persistence of transgene expression can vary among different mouse strains (Barr et al., Gene Ther. 2:151–155, 1995).

The lack of persistence in the expression of adenoviral vector-delivered transgenes may be due to limitations imposed by the choice of promoter or transgene contained in the transcription unit (Guo et al., Gene Ther. 3:802–801, 1996; Tripathy et al., Nature Med. 2:545–550, 1996).

Modifications to the adenoviius genomic sequences contained in the recombinant vector have been attempted in order to decrease the host immune response (Yang et al., Nature Genetics 7:362–369, 1994; Lieber et al., J. Virol. 70:8944–8960, 1996; Gorziglia et al., J. Virol. 70:4173–4178; Kochanek et al., Proc. Natl. Acad. Sci. USA 93:5731–5736, 1996; Fisher et al., Virology 217:11–22, 1996).

In addition to deletions in the adenovirus E1 region, first-generation adenoviral vectors often contain modifications to the E3 region in order to increase the packaging capacity of the vectors and to reduce viral gene expression (Yang et al., J. Virol. 69:2004–2015, 1995; Zsengeller et al., Hum. Gene Ther. 6:457–467, 1995; Brody et al., Hum. Gene Ther. 5:821–836, 1994). However, the adenovirus E3 regions contains certain proteins which modulate the host's antiviral immune response. The E3 transcription unit encodes the 12.5K, 6.7K, gp19K, 11.6K, 10.4K, 14.5K and 14.7K proteins (Wold et al., Trends Microbiol. 2:437–443, 1994). The E3 14.7K, 14.5K, and 10.4K proteins are able to protect infected cells from TNF-induced cytolysis. The adenovirus E3 gp19K protein can complex with MHC Class I antigens and retain them in the endoplasmic reticulum, which prevents cell surface presentation and killing of infected cells by cytotoxic T-lymphocytes (CTLs) (Wold et al., Trends Microbiol. 437–443, 1994), suggesting that its presence in a recombinant adenoviral vector may be beneficial. The E3 11.6K gene (adenovirus death protein) is required for cell lysis and the release of adenovirus from infected cells (Tollefson et al., J. Virol. 70:2296–2306, 1996; Tollefson et al., Virology 220:152–162, 1996).

Earlier designs of adenoviral vectors in which the E3 region was modified have shown only transient expression of a transgene in the lungs of test animals (Yang et al., J. Virol. 69:2004–2015; Zsengeller et al., Hum Gene Ther. 6:457–467, 1995).

Modifications to the adenovirus E4 region have been introduced into adenoviral vectors in order to reduce viral gene expression and to further increase carrying capacity (Armentano et al., Hum. Gene Ther. 6:1343–1353, 1995). However, experiments in which adenoviral vectors were introduced into nude mice demonstrated that the context of the adenovirus E4 genomic region was a determinant in the persistence of expression, especially when the CMV promoter was used to control expression of the transgene (Kaplan et al., Hum. Gene Ther. 8:45–56, 1997; Armentano et al., J. Virol. 71:2408–2416, 1997).

The current state of adenoviral vector-based gene delivery requires the development of novel adenoviral vectors which demonstrate a capability for persistence and sustained expression of a transgene.

SUMMARY OF THE INVENTION

The invention is directed to novel adenoviral vectors which are capable of facilitating persistent expression of a transgene which is delivered by the vector to a cell. The vectors are E1/partial E3 deleted vectors which contain a transgene operably linked to expression control sequences, preferably the CMV promoter. The invention is also directed to compositions comprising the adenoviral vectors of the invention and to methods for providing persistent expression of a transgene to the cells of an individual by administration of the compositions.

DETAILED DESCRIPTION OF THE INVENTION

Figure 1:
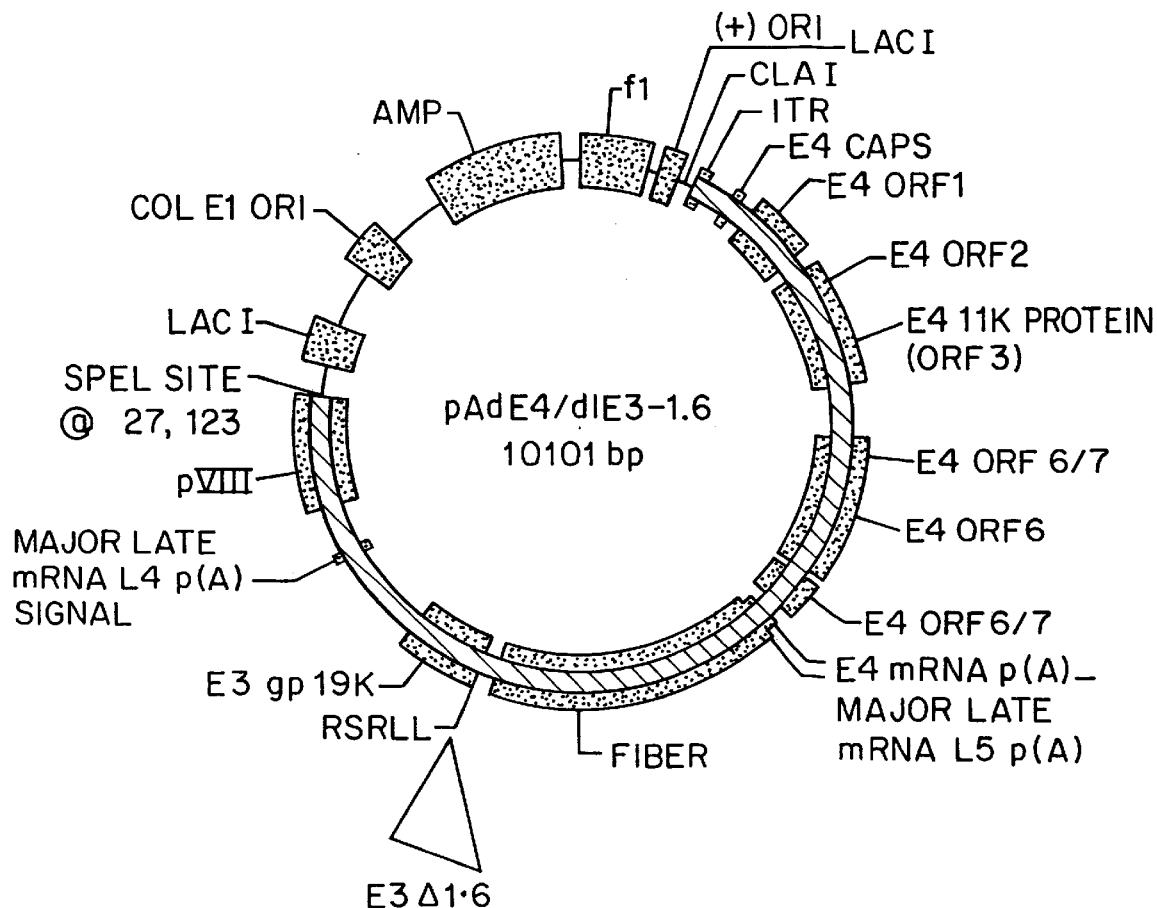
FIG. 1 shows a schematic diagram of pAd/E4+/E3Δ1.6.

The invention is directed to novel adenoviral vectors which are capable of facilitating persistent expression of a transgene that is operably linked to expression control sequence, preferably the cytomegalovirus immediate early (CMV) promoter. These vectors are advantageous in that they provide longer duration of expression of a transgene, thereby reducing the need for repeated administration of a vector to achieve a specific phenotypic result.

The adenoviral vectors of the invention comprise an adenoviral genome which is deleted for all or part of the E1 region and all or part of the E3 region. The adenovirus E4 region is preferably retained in the vector to increase the persistence of expression from a transgene under the control of the CMV promoter.

The adenoviral vectors of the invention are preferably replication-defective, e.g., they are deleted for genes which are essential to autonomous replication of the virus. Such deletions create vectors which are safer for administration to individuals and have the additional advantage that they can carry larger DNA inserts. In a preferred embodiment, the vectors of the invention contain a deletion in the E1 genomic region of the virus which removes the coding sequences for the E1A protein required for autonomous replication and which may remove all or part of the E1B region of the virus genome.

The protein IX coding sequences in the adenovirus genome may be retained in the vectors of the invention in order to optimize packaging capacity. In a particular embodiment of the invention, the protein IX coding sequences may be relocated from their position at the border of the E1 sequences to another location in the adenovirus genome, e.g., into the E4 region of the virus. Such a relocation decreases the ability of these sequences to mediate recombination with homologous adenovirus sequences in packaging cell lines which can result in the generation of replication-competent adenoviruses (RCA) during vector production (Hehir et al., J. Virol. 70:8459–8467, 1996).

The adenoviral vectors of the invention retain all or part of the adenovirus E2 genomic region.

The adenoviral vectors of the invention retain all or part of the adenovirus E4 genomic region. Such sequences appear to facilitate the persistence of transgene expression in nude mice when contained in an adenoviral vector containing a transgene under the control of a CMV promoter (Armentano et al., J. Virol. 71:2408–2416, 1997). Preferably, the adenoviral vectors of the invention retain the coding sequences for the E4 ORF3 gene in order to facilitate persistent transgene expression.

The adenoviral vectors of the invention retain all or part of the adenovirus E3 genomic region. Modifications to the E3 region such as truncations of the E3 coding sequence or deletions that remove particular open reading frames are permissible, providing that these alterations do not interfere with persistent expression of the transgene. Preferably, the modifications to the E3 region retain the gene for the gp19K protein, due to its particular immunomodulatory role in preventing viral antigen presentation, thereby limiting the CTL response to adenovirus-infected cells (Wold et al., Trends Microbiol. 437–443, 1994). The retention of the genes for other immunomodulatory proteins such as 10.4K, 14.5K and 14.7K is also within the scope of the modifications contemplated for the E3 region.

In a preferred embodiment of the invention, the gene for the E3 11.6K protein is not retained in the adenoviral vectors of the invention. This protein is involved in the lysis of adenovirus-infected cells (Tollefson et al., J. Virol. 70:2296–2306, 1996; Tollefson et al., Virology 220:152–162, 1996). Overexpression of E3 open reading frames other than the 11.6K gene may also result in diminishing the effect of the expression of the 11.6K gene.

In a preferred embodiment of the invention, the adenoviral vector is Ad2/CMV/E3Δ1.6, which contains the CMV promoter to which a transgene may be operably linked and further contains an E1 deletion and a partial deletion of 1.6 kb from the E3 region. This is a replication defective vector containing a deletion in the E1 region into which a transgene and its expression control sequences can be inserted, preferably the CMV promoter contained in this vector. It further contains the wild-type adenovirus E2 and E4 regions. The vector contains a deletion in the E3 region which encompasses 1549 nucleotides from adenovirus nucleotides 29292 to 30840 (Roberts, R. J., et al., Adenovirus DNA, in Developments in Molecular Virology, W. Doerfler, ed., 8:1–51, 1986). These modifications to the E3 region in vector Ad2/CMV/E3Δ1.6 result in the following: (a) all the downstream splice acceptor sites in the E3 region are deleted and only mRNA a would be synthesized from the E3 promoter (Tollefson et al., J, Virol. 70:2296–2306, 1996; Tollefson et al., Virology 220:152–162, 1996); (b) the E3A poly A site has been deleted, but the E3B poly A site has been retained; (c) the E3 gp19K (MHC I binding protein) gene has been retained; and (d) the E3 11.6K (Ad death protein) gene has been deleted.

The adenoviral vectors of the invention can utilize adenovirus genomic sequences from any adenovirus serotypes, including but not limited to, adenovirus serotypes 2, 5, and all other preferably non-oncogenic serotypes.

The adenoviral vectors of the invention may contain a transgene that is within a transcription unit which allows persistent expression of the transgene. Persistent expression by an adenoviral vector of the invention is defined as generating a sustained level of expression of a transgene over time.

Transgene is defined herein as any gene that is not native to the adenovirus genome.

The transcription unit of the adenoviral vectors of the invention is defined herein as the DNA sequences encoding a transgene, any expression control sequences such as a promoter or enhancer, a polyadenylation element, and any other regulatory elements that may be used to modulate or increase expression, all of which are operably linked in order to allow expression of the transgene. The use of any expression control sequences which facilitate persistent expression of the transgene is within the scope of the invention. Such sequences or elements may be capable of generating tissue-specific expression or may be inducible by exogenous agents or stimuli.

Preferably, the cytomegalovirus (CMV) immediate early promoter (Boshart et al., Cell 41:521–530, 1985) is used to control expression of the transgene in a transcription unit, or a truncated fragment of this promoter which functions analogously may be used. The CMV promoter is positioned 5' to the transgene in a transcription unit. Portions of the full-length promoter can be tested for their ability to allow persistent expression of a transgene using assays described below. In a preferred embodiment, the CMV promoter region from nucleotides –523 to –14 is used in an adenoviral vector of the invention.

Polyadenylation signals which may be positioned at the 3' end of the transgene in a transcription unit include, but are not limited to, those derived from bovine growth hormone (BGH) and SV40.

Transgenes which can be delivered and expressed from a transcription unit in the adenoviral vectors of the invention include, but are not limited to, those encoding enzymes, blood derivatives, hormones, lymphokines such as the interleukins and interferons, coagulants, growth factors, neurotransmitters, tumor suppressors, apoliproteins, antigens, and antibodies, and other biologically active proteins. Specific transgenes which may be encoded by the transcription units of the invention include, but are not limited to, cystic fibrosis transmembrane regulator (CFTR), dystrophin, glucocerebrosidase, tumor necrosis factor, p53, retinoblastoma (Rb), and adenosine deaminase (ADA). Transgenes encoding antisense molecules or ribozymes are also within the scope of the invention.

The transcription unit can be inserted into an adenoviral vector of the invention in any site from which expression of the transgene is possible. Preferably, the transcription unit is inserted into the E1 deletion in an adenoviral vector of the invention.

In a particularly preferred embodiment of the invention, the adenoviral vector is Ad2/CMV–CFTR/E3Δ1.6, containing the gene for the cystic fibrosis transmembrane regulator protein (CFTR) operably linked to the CMV promoter and inserted into the deleted E1 region, and also containing a 1.6 kb deletion from the E3 region, which is capable of facilitating persistent expression of the CFTR transgene in the cells of an individual to which it is administered.

To create the recombinant adenoviral vectors of the invention which contain a transcription unit, a plasmid containing the transcription unit inserted into an adenovirus genomic fragment is co-transfected with a linearized viral genome derived from an adenoviral vector of interest into a recipient cell under conditions whereby homologous recombination occurs between the genomic fragment and the virus. Preferably, the transcription unit is engineered into the site of an E1 deletion. As a result, the transcription unit encoding a desired transgene is inserted into the adenoviral genome at the site in which it was cloned into the plasmid, creating a recombinant adenoviral vector. Following the homologous recombination, the vector genome is encapsidated into virions as evidenced by the formation of viral plaques. Preparation of replication-defective vector stocks can be accomplished using cell lines that complement viral genes deleted from the vector, e.g., 293 or A549 cells containing the deleted adenovirus E1 genomic sequences. After amplification of plaques in suitable complementing cell lines, the viruses can be recovered by freeze-thawing and subsequently purified using cesium chloride centrifugation. Alternatively, virus purification can be performed using chromatographic techniques (e.g., as set forth in International Application No. PCT/US96/13872, filed Aug. 30, 1996, incorporated herein by reference).

Titers of replication-defective adenoviral vector stocks can be determined by plaque formation in a complementing cell line, e., 293 cells. For example, end-point dilution using an antibody to the adenoviral hexon protein may be used to quantitate virus production (Armentano et al., Hum. Gene Ther. 6:1343–1353, 1995).

Assays may be performed in tissue culture systems to determine the persistence of expression of a transgene. Cell lines which may be infected with the adenoviral vectors of the invention are suitable for assays which measure the level and duration of expression of a contained transgene. The transgene may encode a biologically useful protein or may encode a marker protein used to test the ability of the adenoviral vector to deliver a transgene which is capable of persistent expression. Relevant molecular assays to determine the persistence of expression include the measurement of transgene mRNA, by, for example, Northern blot, S1 analysis or reverse transcription-polymerase chain reaction (RT-PCR). The presence of a protein encoded by a transgene may be detected by Western blot, immunoprecipitation, immunocytochemistry, or other techniques known to those skilled in the art.

In order to determine the persistence of transgene expression using the invention, animal models are particularly relevant in order to assess transgene persistence over time against a background of potential host immune response. Such an animal model may be chosen with reference to such parameters as ease of delivery of the adenoviral vector, identity of transgene, relevant molecular assays, and potential for assessment of clinical status. Where the transgene encodes a biologically active protein, an animal model which is representative of a disease state that responds to the provision of such a protein may optimally be used in order to assess clinical improvement.

Relevant animals in which the adenoviral vectors of the invention may be assayed include, but are not limited to, mice, rabbits, rats and monkeys. Suitable mouse strains in which the adenoviral vectors of the invention may be tested include, but are not limited to, C3H, C57B1/6 (wild-type and nude) and Balb/c (available from Taconic Farms, Germantown, N.Y.).

Where it is desirable to assess the host immune response to vector administration, testing in immune-competent and immune-deficient animals may be compared in order to define specific adverse responses generated by the immune system. The use of immune-deficient animals, e.g., nude mice, may be used to characterize vector performance and transgene expression independent of an acquired host response, and to identify other determinants of transgene persistence.

Specific parameters of a host immune response in immune-competent animal models or treated individuals may be determined after vector administration in order to determine the magnitude of the host immune response. Both humoral and cell mediated immune responses may be determined. Relevant assays for cell mediated host immune responses include T cell proliferation assays and CTL assays (Kaplan et al., Gene Ther. 3:117–127, 1996) from cells isolated from the spleens of treated animals. The infiltration of T cells into an infected site is also indicative of a host immune response (Ginsberg et al., Proc. Natl. Acad. Sci. USA 88:1651–1655, 1991). The level of anti-adenovirus antibodies or anti-transgene antibodies in serum and other fluids can be measured to assess the host humoral response to the administration of the vector, using standard immunological techniques.

In a particular embodiment where the transgene in an adenoviral vector is CFTR which is administered to the respiratory epithelium of test animals, persistence of expression of CFTR may be assayed in the lungs of relevant animal models, for example, C57B1/6 or Balb/c mice, cotton rats, or Rhesus monkeys. Molecular markers which may used to determine the persistence of expression include the measurement of CFTR mRNA, by, for example, Northern blot, S1 analysis or RT-PCR. The presence of the CFTR protein may be detected by Western blot, immunoprecipitation, immunocytochemistry, or other techniques known to those skilled in the art.

The adenoviral vectors of the invention may be engineered to express a surface molecule that facilitates targeting specific cell types, e.g., an adenoviral fiber or penton protein modified to interact with a specific cell surface receptor. Although adenoviral vectors may be most frequently introduced to a cell by infection, other forms of delivery of the vectors disclosed herein are within the scope of the invention, e.g., using cationic amphiphiles complexed with the adenoviral vectors of the invention to mediate delivery to cells. Cationic amphiphiles have a chemical structure encompassing polar and non-polar domains wherein the polar domain attaches to a biologically useful molecule and the non-polar domain facilitates entry of such a molecule across a lipid membrane. Preferred cationic amphiphiles for such delivery are described in PCT Publication No. WO96/18372, published Jun. 20, 1996, incorporated herein by reference.

The adenoviral vectors of the invention can be used to deliver and express any number of transgenes to cells in order to achieve a specific phenotypic result.

The present invention is further directed to compositions containing the adenoviral vectors of the invention which can be administered in an amount effective to deliver one or more desired transgenes to the cells of an individual in need of such transgenes so as to provide persistent expression of a transgene encoding a biologically active protein.

The compositions can include physiologically acceptable carriers, including any relevant solvents. As used herein, "physiologically acceptable carrier" includes any and all solvents, dispersion media, coatings, antibacterial and antifungal agents, isotonic and absorption delaying agents, and the like. Except insofar as any conventional media or agent is incompatible with the active ingredient, its use in the compositions of the invention is contemplated.

Routes of administration for the compositions containing the adenoviral vectors include conventional and physiologically acceptable routes such as direct delivery to the target organ or tissue, intranasal, intravenous, intramuscular, subcutaneous, intradermal, oral and other parenteral routes of administration.

The invention is further directed to methods for using the compositions of the invention in vivo or ex vivo applications in which it is desirable to deliver one or more transgenes into cells using the adenoviral vectors of the invention so as to provide persistent expression of a transgene encoding a biologically active protein. In vivo applications involve the direct administration of an adenoviral vector of the invention formulated into a composition to the cells of an individual. Ex vivo applications involve the transfer of the adenoviral vector directly to harvested autologous cells which are maintained in vitro, followed by readministration of the transduced cells to a recipient.

Dosage of an adenoviral vector of the invention which is to be administered to an individual to provide persistent expression of a transgene encoding a biologically active protein is determined with reference to various parameters, including the condition to be treated, the age, weight and clinical status of the individual, and the particular molecular defect requiring the provision of a biologically active protein. The dosage is preferably chosen so that administration causes persistent expression of the transgene and a specific phenotypic result, as measured by molecular assays or clinical markers. For example, determination of the persistence of expression of a transgene encoded by an adenoviral vector of the invention containing the CFTR transgene which is administered to an individual can be performed by molecular assays including the measurement of CFTR mRNA, by, for example, Northern blot, S1 or RT-PCR analysis or the measurement of the CFTR protein as detected by Western blot, immunoprecipitation, immunocytochemistry, or other techniques known to those skilled in the art. Relevant clinical studies which could be used to assess a specific phenotypic result from delivery of the CFTR transgene include PFT assessment of lung function and radiological evaluation of the lung. Demonstration of the delivery of a transgene encoding CFTR can also be demonstrated by detecting the presence of a functional chloride channel in cells of an individual with cystic fibrosis to whom the vector containing the transgene has been administered (Zabner et al., J. Clin. Invest. 97:1504–1511, 1996; allowed U.S. patent application Ser. No. 08/136,742, filed Oct. 13, 1993, now U.S. Pat. No. 5,670,488, incorporated herein by reference). The persistence of transgene expression in other disease states can be assayed analogously, using the specific clinical parameters most relevant to the condition.

Dosages of an adenoviral vector of the invention which can be used in providing a transgene contained in a vector to an individual for persistent expression of a biologically active protein encoded by the transgene and to achieve a specific phenotypic result range from approximately $10^8$ infectious units (I.U.) to $10^{11}$ I.U. for humans.

It is especially advantageous to formulate parenteral compositions in dosage unit form for case of administration and uniformity of dosage. Dosage unit form as used herein refers to physically discrete units suited as unitary dosages for the subjects to be treated, each unit containing a predetermined quantity of active ingredient calculated to produce the specific phenotypic result in association with the required physiological carrier. The specification for the novel dosage unit forms of the invention are dictated by and directly depend on the unique characteristics of the adenoviral vector used in the formulation and the limitations inherent in the art of compounding. The principal active ingredient (the adenoviral vector) is compounded for convenient and effective administration with the physiologically acceptable carrier in dosage unit form as discussed above.

Maximum benefit and achievement of a specific phenotypic result from the administration of an adenoviral vector of the invention to deliver one or more transgenes to an individual may require repeated administration. Such repeated administration may involve use of the same adenoviral vector, or, alternatively, may involve the use of different vectors engineered to carry the same transgene but which are rotated in order to alter viral antigen presentation and decrease host immune response.

The practice of the invention employs, unless otherwise indicated, conventional techniques of protein chemistry, molecular virology, microbiology, recombinant DNA technology, and pharmacology, which are within the skill of the art. Such techniques are explained fully in the literature. See. e.g., *Current Protocols in Molecular Biology*, Ausubel et al., eds., John Wiley & Sons, Inc., New York, 1995, and *Remington's Pharmaceutical Sciences*, 17th ed., Mack Publishing Co., Easton, Pa., 1985.

The invention is further illustrated by the following specific examples which are not intended in any way to limit the scope of the invention.

EXAMPLE 1

Construction of AD2/CMV–CFTR/E3Δ1.6

The recombinant adenoviral vector Ad2/CMV–CFTR/E3Δ1.6 was generated by homologous recombination between the plasmid pAd/E4+/E3Δ1.6 (FIG. 1) and viral DNA isolated from the Ad2/CFTR-5 virus. Ad2/CFTR-5 contains human CFTR (hCFTR) as the transgene under the control of the CMV promoter (nucleotides −523 to −14, Boshart et al., Cell 41:521–530, 1985) and the BGH polyA signal, which is inserted at the site of a deletion in the E1 region. The E2 and E3 regions of Ad2/CFTR-5 contain wild-type adenovirus serotype 2 sequences (Ad2) and all E4 sequences have been deleted except for E4ORF6. Plasmid pAd/E4+/E3Δ1.6 contains the right hand end of adenovirus 2 from the SpeI site at nucleotide 27123 until the right inverted terminal repeat (ITR). The E3 region contains a 1549 bp deletion (Ad2 nucleotides 29292 to 30840).

Ad2/CFTR-5 DNA was cleaved at the unique PacI site at Ad2 nucleotides positions 28612. Plasmid pAd/E4$^+$/E3Δ1.6 was linearized by cleaving at the unique ClaI site which is immediately downstream of the ITR. These two DNAs were used to co-transfect 293 cells by the CaPO$_4$ precipitation method. Viral plaques were isolated, expanded and recombinant viruses identified by restriction digestion of total DNA from virally infected cells.

Figure 2:
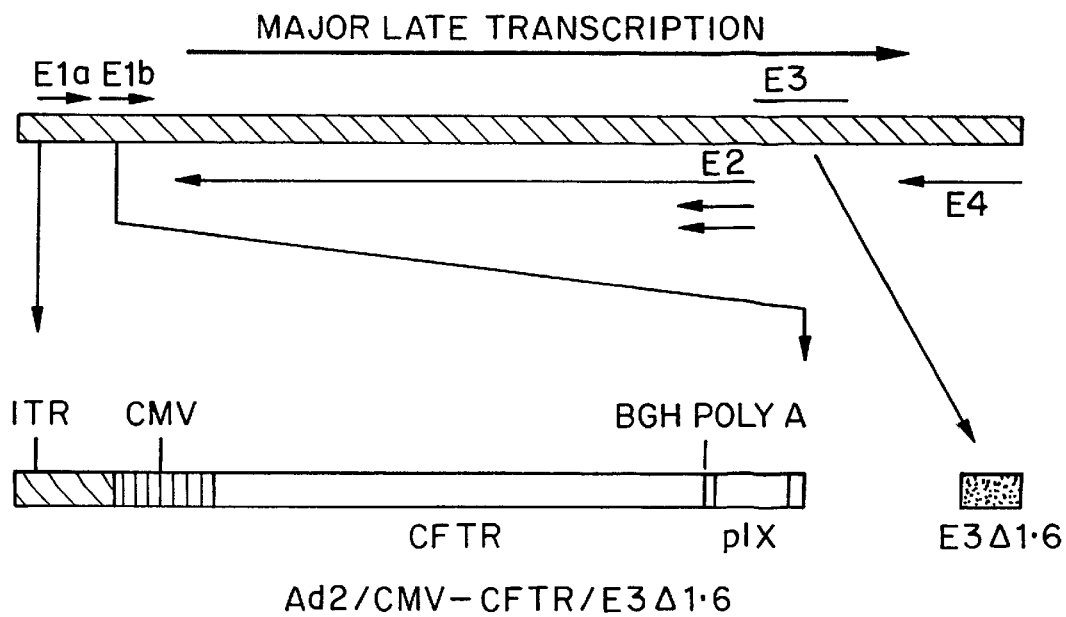
FIG. 2 shows a schematic diagram of the Ad2/CMV-CFTR/E3Δ1.6 vector.
Figure 3:
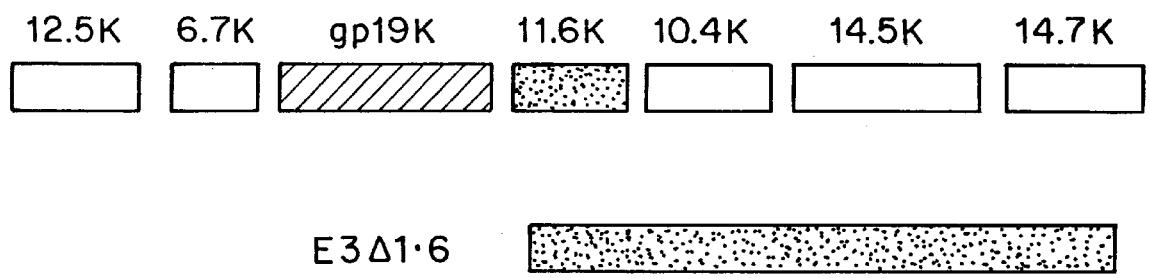
FIG. 3 shows a schematic diagram of the E3 modifications to the Ad2/CMV-CFTRJE3Δ1.6 vector.

The Ad2/CMV–CFTR/E3Δ1.6 virus that results from this recombination contains wild-type E2 and E4 regions (FIG. 2) and has the 1549 bp E3 deletion. The extent of the modification to the E3 region is shown in FIG. 3.

EXAMPLE 2

Persistent Transgene Expression in Immunecompetent and Nude Mice

Methods

C57B1/6 (wild-type and nude) and BALB/c mice were purchased from Taconic Farms (Germantown, N.Y.) and instilled with the vector Ad2/CMV–CFTR/E3Δ1.6 using approximately $2 \times 10^9$ infectious units (I.U.) by the intranasal route. RNA was isolated as described below and the levels of human CFTR (hCFTR) expression was determined at different time points by quantitative RT-PCR.

Tissue samples from the lungs of each mouse were homogenized in RNA Stat-60 solution (Tel-Test B, Inc). RNA was extracted according to the acid guanidinium/phenolchloroform method (Chomczynski et al., Anal. Biochem. 162:156–159, 1987) in a Mini-Beadbeater (Biospec Corp, Bartlesville, Okla.). RNA samples were pooled for animals in each group per time point.

Total RNA (7.5 mg) was subjected to DNase treatment. In addition to the sample RNA, $10^3$ or $10^2$ molecules of synthetic competitive RNA (a 469 bp CAT transcript with CFTR sequences at both ends) were added to the reaction mix. Reverse transcription was performed with a cDNA kit from Invitrogen (San Diego, Calif.). Following reverse transcription, cDNA from each test group was amplified using conditions and reagent concentrations as stated above for the PCR reaction. The PCR product from the hCFTR sequence is 544 bp; the competitor product is 469 bp. The ratio of the intensity of the products was compared to those of a DNA standard curve containing log concentrations of Ad2/CFTR-8 DNA (Hehir et al., J. Virol. 70:8459–8467, 1996) (from $10^1$ to $10^6$) run with the appropriate number of copies of competitor DNA to quantitate gene expression.

Results

Figure 4:
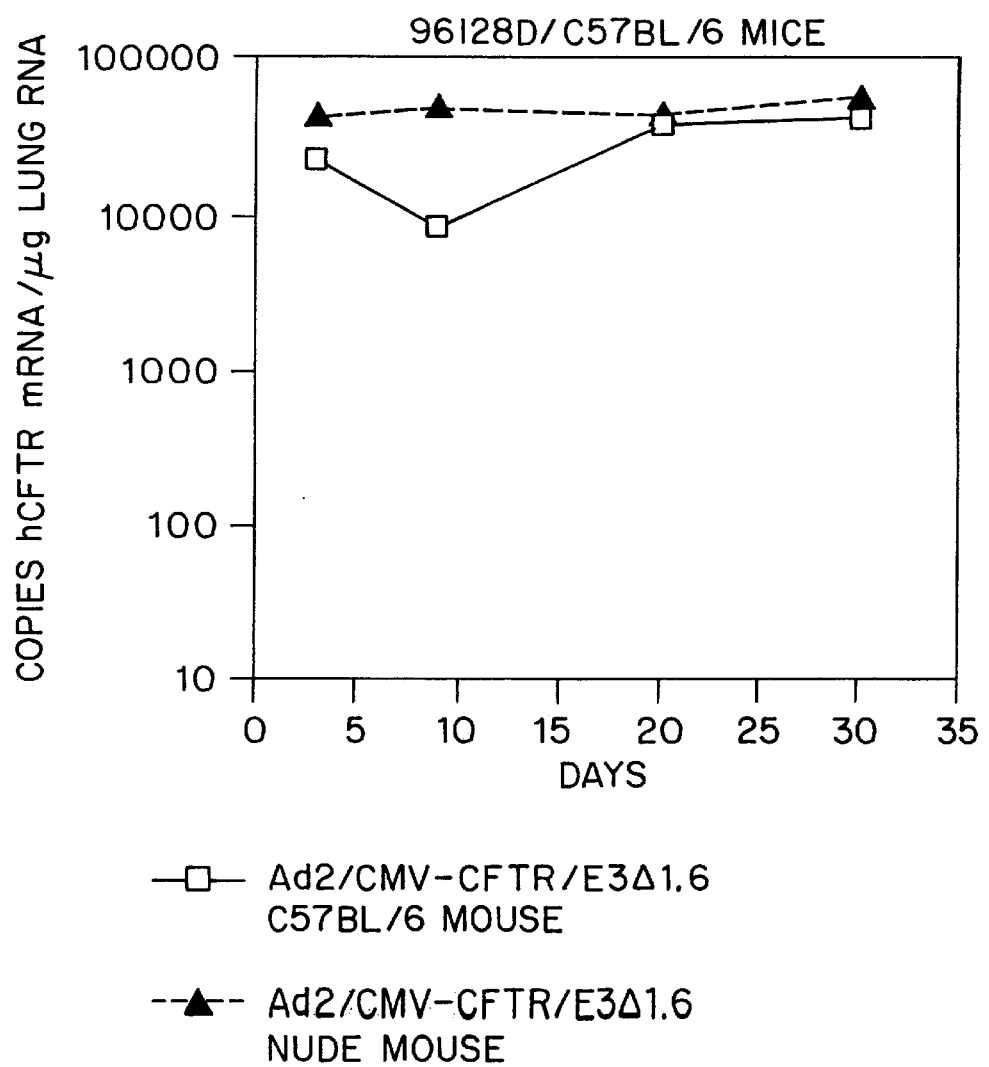
FIG. 4 shows expression of human CFTR from the Ad2/CMV-CFTR/E3Δ1.6 vector in the lungs of immune-competent and nude C57B1/6 mice.

As shown in FIG. 4, Ad2/CMV–CFTR/E3Δ1.6 gave rise to persistent expression of hCFTR up to 30 days in nude C57Bl/6 mice and in immune-competent C57Bl/6 mice.

Figure 5:
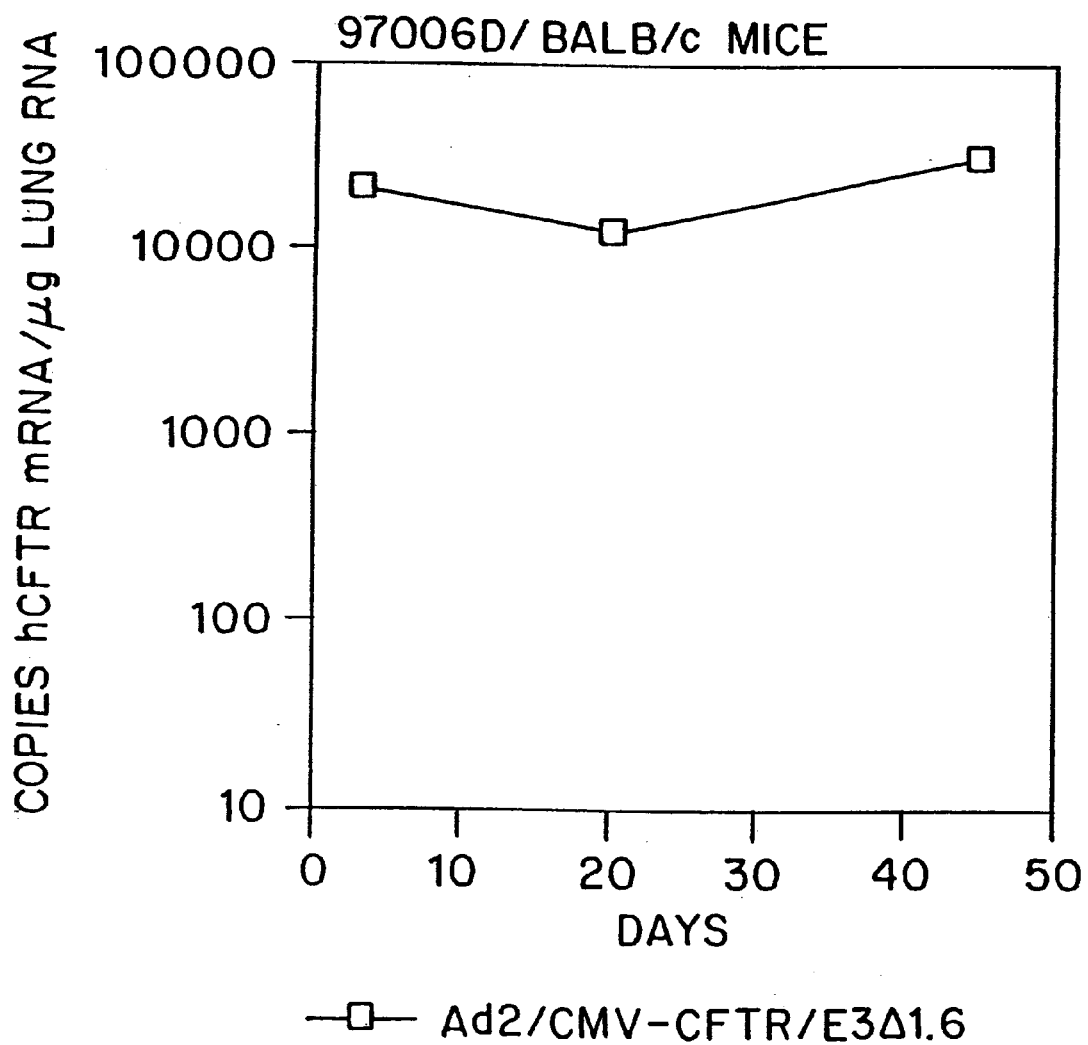
FIG. 5 shows expression of human CFTR from the Ad2/CMV-CFTR/E3Δ1.6 vector in the lungs of immune-competent Balb/c mice.

In immune-competent BALB/c mice, persistent expression of hCFTR provided by Ad2/CMV–CFTR/E3Δ1.6 was observed up to day 45 (FIG. 5), and has been further observed to persist to day 70 (data not shown). Such persistent expression of hCFTR in the lungs of immune-competent animals has not been observed in previous studies beyond 2–3 weeks using first generation ($E2^+$, $E4^+$) adenoviral vectors.

We claim:

1. An adenoviral vector, Ad2/CMV/E3Δ1.6, comprising an adenoviral genome from which nucleotides 29292 through 30840 of the adenoviral E3 region have been deleted, and additionally comprising a heterologous nucleic acid operably linked to expression control sequences comprising a cytomegalovirus promoter inserted into said adenoviral genome, wherein the Ad2/CMV/E3Δ1.6 vector provides for persistent expression of the heterologous nucleic acid in a target cell.

2. The vector of claim 1, wherein the heterologous nucleic acid encodes human cystic fibrosis transmembrane conductance regulator (CFTR) protein.

3. The vector of claim 2, which is Ad2/CMV–CFTR/E3Δ1.6.

* * * * *